United States Patent
Huth-Fehre et al.

(10) Patent No.: US 6,262,419 B1
(45) Date of Patent: Jul. 17, 2001

(54) PROCESS AND DEVICE FOR RECOGNIZING ORGANIC SUBSTANCES

(75) Inventors: Thomas Huth-Fehre; Frank Kowol; Roger Feldhoff; Thomas Kantimm, all of Münster (DE)

(73) Assignee: Institut fuer Chemo-und Biosensorik Muenster E.V. (DE)

( * ) Notice: Subject to any disclaimer, the term of this patent is extended or adjusted under 35 U.S.C. 154(b) by 0 days.

(21) Appl. No.: 09/101,489
(22) PCT Filed: Jan. 10, 1997
(86) PCT No.: PCT/DE97/00060
§ 371 Date: Sep. 1, 1998
§ 102(e) Date: Sep. 1, 1998
(87) PCT Pub. No.: WO97/25605
PCT Pub. Date: Jul. 17, 1997

(30) Foreign Application Priority Data

Jan. 12, 1996 (DE) .............................................. 196 01 923

(51) Int. Cl.⁷ ................................................. G01N 21/35
(52) U.S. Cl. ................................. 250/341.8; 250/339.06; 250/227.23
(58) Field of Search ........................... 250/341.8, 227.23, 250/339.08, 339.06, 339.11, 338.4

(56) References Cited

U.S. PATENT DOCUMENTS

| | | | |
|---|---|---|---|
| 4,254,337 | * 3/1981 | Yasujima et al. | 250/339.06 |
| 4,631,408 | * 12/1986 | Zelmanovic et al. | 250/339.11 |
| 4,880,979 | * 11/1989 | Yoshida | 250/338.4 |
| 4,883,963 | * 11/1989 | Kemeny et al. | 250/339.11 |
| 5,216,484 | 6/1993 | Chao et al. . | |
| 5,510,619 | * 4/1996 | Zachmann et al. | 250/339.08 |
| 5,747,806 | * 5/1998 | Khalil et al. | 250/339.09 |
| 5,841,546 | * 11/1998 | Carangelo et al. | 250/227.23 |

FOREIGN PATENT DOCUMENTS

| | | |
|---|---|---|
| 43 40 914 A1 | 6/1995 | (DE) . |
| 0 250 070 A1 | 12/1987 | (EP) . |
| 2 217 838 | 11/1989 | (GB) . |
| WO 94/11126 | 5/1994 | (WO) . |

* cited by examiner

Primary Examiner—Constantine Hannaher
Assistant Examiner—Otilia Gabor
(74) Attorney, Agent, or Firm—Marshall & Melhorn, LLC

(57) ABSTRACT

In a process for recognizing organic substances in solids by measuring the spectrum of the radiation which is reflected or transmitted, radiation with a wavelength between 2–4 μm is used and, for radiation of solids, unmodulated radiation is used. The radiation source should have an output of at least 50 W and the distance between the illumination optics from the solid being investigated should be at least 10 cm. Recognition is based on absorption bands of the extended oscillations of C—H bonds and sometimes the presence of absorption bands of N—H bonds. Broad band radiation is preferable for radiation of the solids, and the reflected or transmitted radiation is directed through a narrow band filter with adjustable transmission frequency. This can be advantageously formed with an acousto-optical filter.

19 Claims, 6 Drawing Sheets

PROCESS AND DEVICE FOR RECOGNIZING ORGANIC SUBSTANCES

TECHNICAL FIELD

The invention relates to a method according to the preamble to claim 1 and to a device for carrying out this method.

BACKGROUND ART

On-line measuring technology preferably makes use of NIR spectrometry, which is capable of operating rapidly and also without contact. However, for some applications this wavelength range is not suitable, e.g. if carbon black or graphite are used as pigments, when the method is to be surface sensitive or when foreign atoms, such for example as nitrogen, are to be recognized. In these cases operation must be at wavelengths of greater than 2.5 $\mu$m, i.e. in MIR. In this range Fourier transformation infra-red (FTIR) spectrometers are the means used until now for selection. By means of FTIR spectrometers however only full spectra can be recorded over a wide wavelength range of about 2.5–25 $\mu$m. This requires a relatively long measuring period. In this wavelength range also the room temperature background radiation (about 10 $\mu$m), is found, whose influence can only be suppressed by expensive measures such as cooled diaphragms and filters or by modulation of the illuminating radiation. FTIR spectrometers also use moving parts, so that their range of applicability is restricted. Furthermore it is difficult to use them at a large distance from the substances to be investigated. Finally, their manufacturing costs are also extremely high.

A method for routine identification of the material of plastic parts with the aid of infra-red spectroscopy is already known from DE 43 40 914 A1. In this case an infra-red reflection spectrum is recorded from the surface of a plastic part to be investigated, and is compared with a set of reference spectra. The reflection spectrum used lies in the MIR range at a wave number range between 400 and 4000 cm$^{-1}$. This area still partly lies in the range of heat radiation. In order that this has no disturbing effect on the measuring procedure, it is necessary to modulate the radiation before it impinges on the plastic part. According to DE 43 40 914 A1, an interferometer is used for this purpose, in which the radiation emitted by an IR light source is subjected to intensity modulation. The optical transmission of such an interferometer is however limited and the power of its output radiation is low in relation to the power of its input radiation. Therefore the output radiation lies at only a few watts, so that the signal-to-noise ratio is low. In order however to be able to investigate carbon-containing plastics in a routine manner by radiation in the MIR range, the document DE 43 40 914 A1 proposes to position the plastic part to be investigated with the aid of a video device. In this way it can be assured that the plastic part is located in a correct measuring position.

Thus however the known method has the disadvantages that it requires an expensive device for positioning, and that it operates relatively slowly due to the positioning procedure.

If a surface irradiator is used as a radiation source, it can be operated at a maximum temperature of 1000° C. Therefore an increase in power can only be achieved by corresponding enlargement of its surface area. This is difficult in the case of a subsequently-incorporated interferometer, so that for this reason the radiation power is restricted to a maximum of 50 watts.

SUMMARY OF THE INVENTION

It is therefore the object of the present invention to indicate a method and a device for recognizing organic substances in solid bodies by spectral detection of radiation reflected or transmitted from the substances, by means of which a rapid measurement is possible and which is versatile and may be used extremely cost-effectively and at a larger distance from the object to be measured.

This object is achieved according to the invention by the feature given in the characterizing part of claim 1.

Advantageous further developments of the method according to the invention and devices for carrying out this method will become apparent from the sub-claims.

By virtue of the fact that a wavelength range of about 2.4–4 $\mu$m is used for radiation, only an extremely restricted wavelength range is used for the investigation, whose information content however surprisingly proves sufficient for many applications. This wavelength range is at a clear distance from the disturbing heat radiation, so that the radiation impinging on the solid body can be unmodulated. Therefore there is no longer any necessity for an interferometer or spectrometer between the radiation source and the solid body to be investigated. As the power restriction caused by this is eliminated, the solid body can be illuminated at a high radiation power, which can extend into the kilowatt range. Due to this high power, positioning of the solid body is omitted, and these can even be scanned in a moving condition, this scanning being without contact and from a larger distance, for example with a distance of 50 cm between the radiation source and the solid body. In this way the measurement can be carried out rapidly, so that it is suitable for on-line operation.

More sensitive detectors may also be used, which likewise contribute to rapid measurement. As in the wavelength range below 4 $\mu$m the room temperature background radiation is still relatively negligible, no special measures are necessary to suppress it.

The output power of the radiation source should come to at least 50 watts and its spacing from the solid body investigated in the case of direct irradiation should be at least 10 cm. In order to compensate for surface irregularities in the solid body, the irradiated surface thereon should come to at least 1 cm$^2$, or should have a minimum diameter of 1 cm.

The method according to the invention is particularly suitable for sorting articles of various plastics, which are moved past the radiation source on a continuously driven conveyor belt.

Within the named wavelength range, recognition is carried out with reference to the absorption bands of the extension oscillations of C—H-bonds and any present extension oscillations of N—H-bonds. In many cases of application these may be clearly distinguished from one another, so that they are sufficient for perfect recognition of specific organic substances.

As light sources emitting in a narrow band with a wavelength range of 2–4 $\mu$m are scarcely obtainable or are difficult to produce, it is appropriate in order to irradiate the substances to be recognized, to use a wide-band radiation and to pass the radiation reflected from or transmitted by the substances through a narrow-band filter whose transmittance frequency is preferably variable. Suitable for this is an acousto-optical filter, which can consist of a TeO$_2$-crystal, upon which is secured an oscillator crystal (piezo-crystal). This latter may be advantageously energized by a digitally programmable high frequency source in order to pass through the transmission wavelength range of about 2–4 $\mu$m.

BRIEF DESCRIPTION OF THE DRAWINGS

The invention will be explained in more detail in the following with reference to embodiments given by way of example and shown in the drawings. Shown are.

DETAILED DESCRIPTION OF THE PREFERRED EMBODIMENTS

Figure 1:
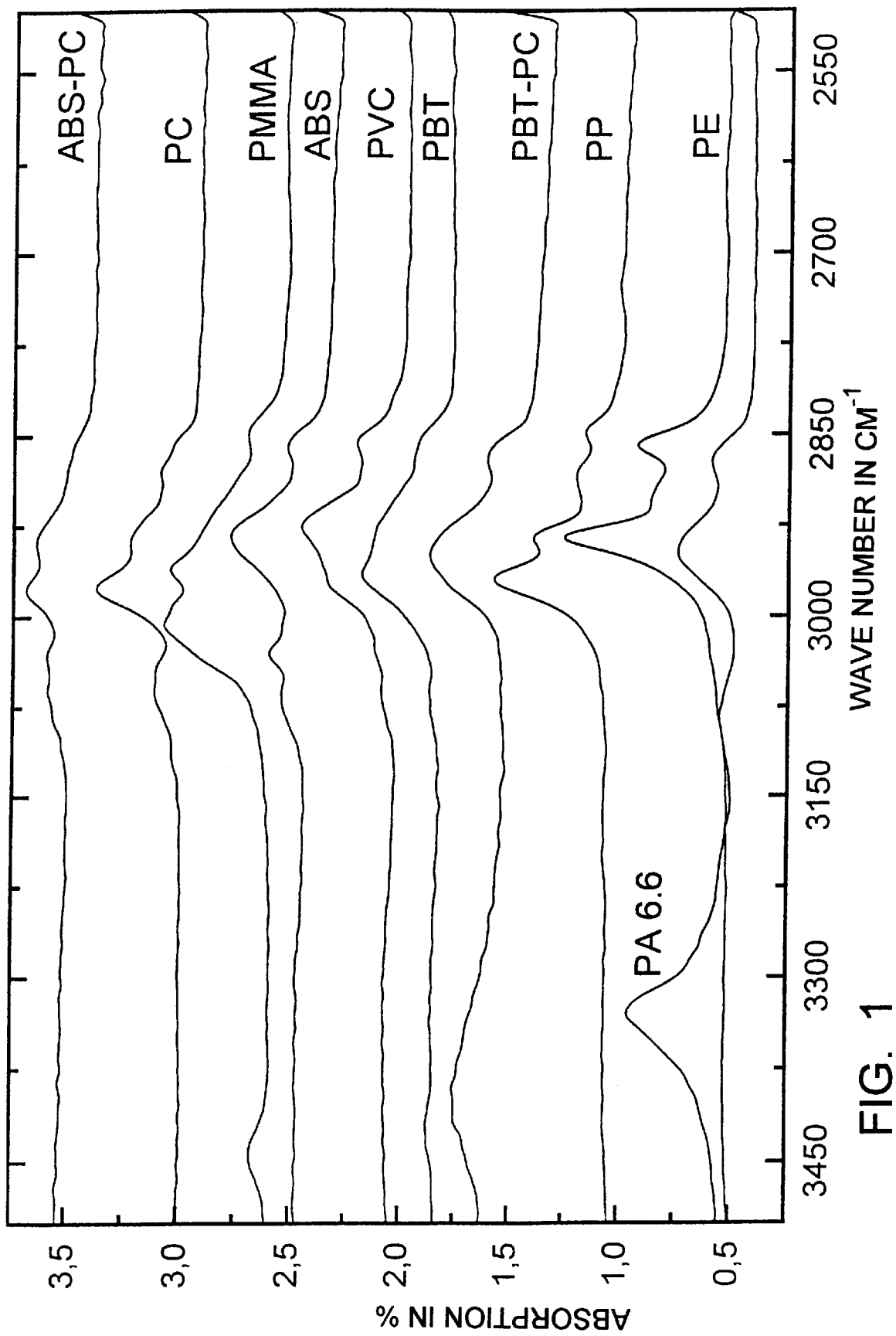
FIG. 1: absorption spectra of various plastics.

FIG. 1 shows spectra of the median infra-red range (MIR) for ten variously blackened plastics, as are often used in the motor vehicle industry. The range shown lies between 2.5 and 3.5 $\mu$m, in which the absorption bands of the C—H extension oscillations (about 3.2–3.6 $\mu$m) or of the N—H extension oscillations (about 2.8–3.1 $\mu$m) of the respective polymer occur. Due to the clear differences between the spectra shown in this narrow wavelength range, it is possible without difficulty to undertake clear identification of the main components of the respective plastics.

Figure 2:
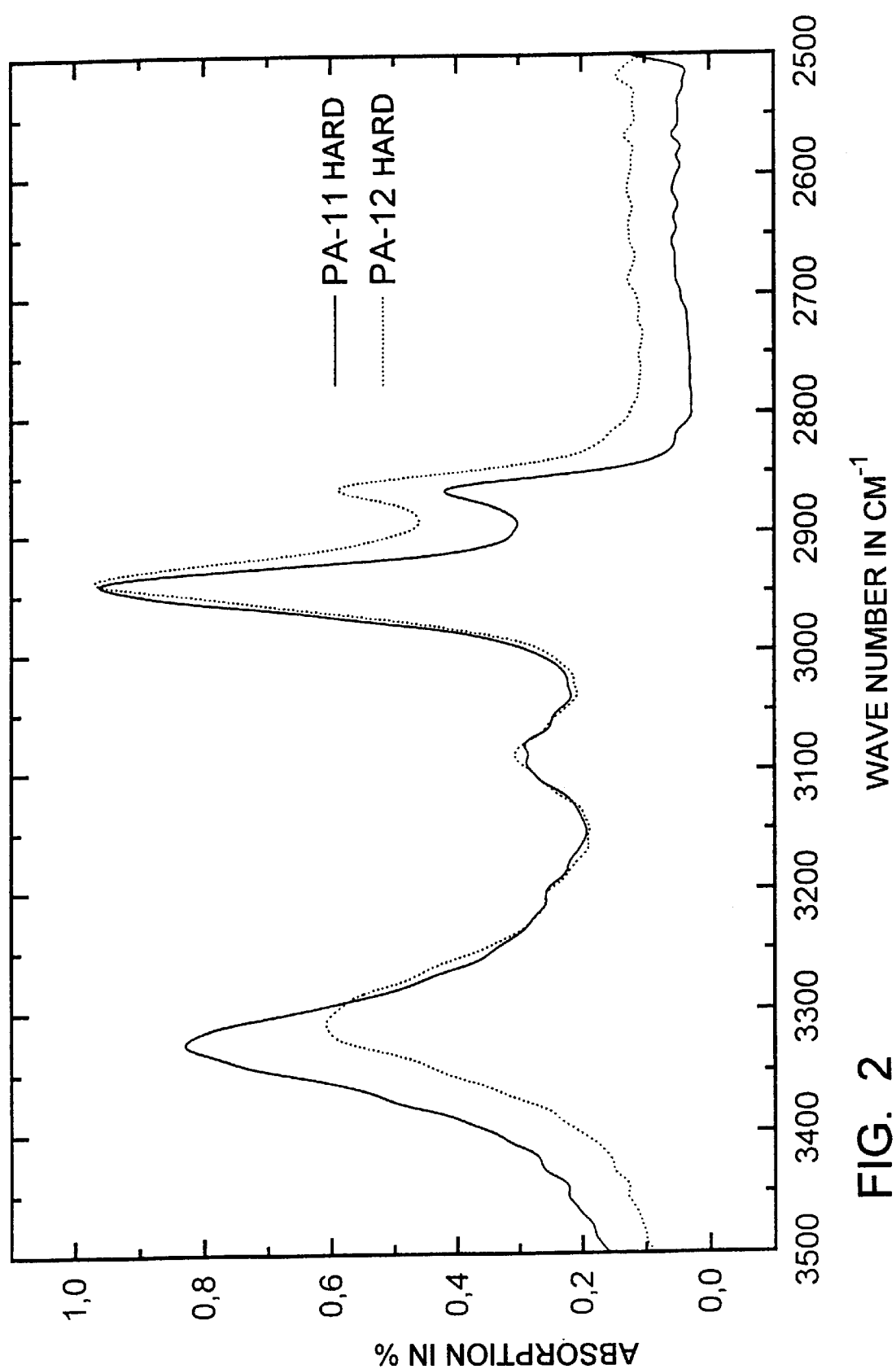
FIG. 2: absorption spectra of polyamide-11 and polyamide-12.

FIG. 2 shows the spectra for a specific polymer, i.e. polyamide, which can be produced in various chain lengths (PA 11 and PA 12) in the wavelength range of 2.5–3.5 $\mu$m. The spectra show clearly recognizable differences, particularly at 2.9 $\mu$m and at 3.3 $\mu$m. If both spectra are standardized to one wavelength, at which both materials have the same absorption, differentiation with reference to the mentioned wavelength ranges is possible.

Figure 3:
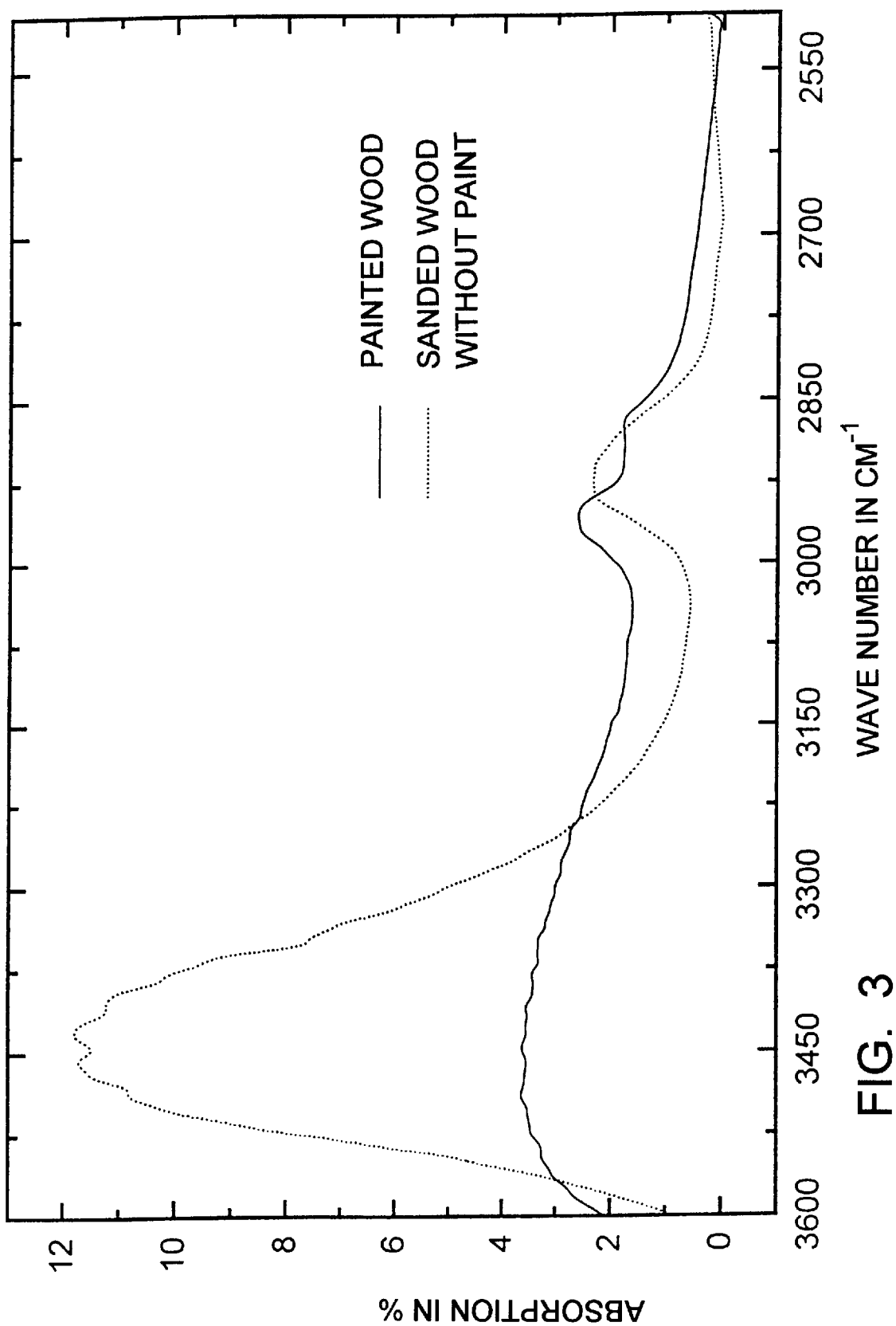
FIG. 3: absorption spectra of painted and unpainted wood.

FIG. 3 shows the absorption spectra of painted and unpainted wood in a wavelength range of 2.5–4.0 $\mu$m. Clear differences occur in two ranges, i.e. between 3.2 and 3.6 $\mu$m, where a relatively intense alteration in the absorption, particularly in the case of unpainted wood, can be observed, and at about 3.0 $\mu$m, where there is an absorption band for painted wood, which is not present in the case of unpainted wood. Thus even painted and unpainted or untreated wood can be differentiated from one another in this wavelength range.

Figure 4:
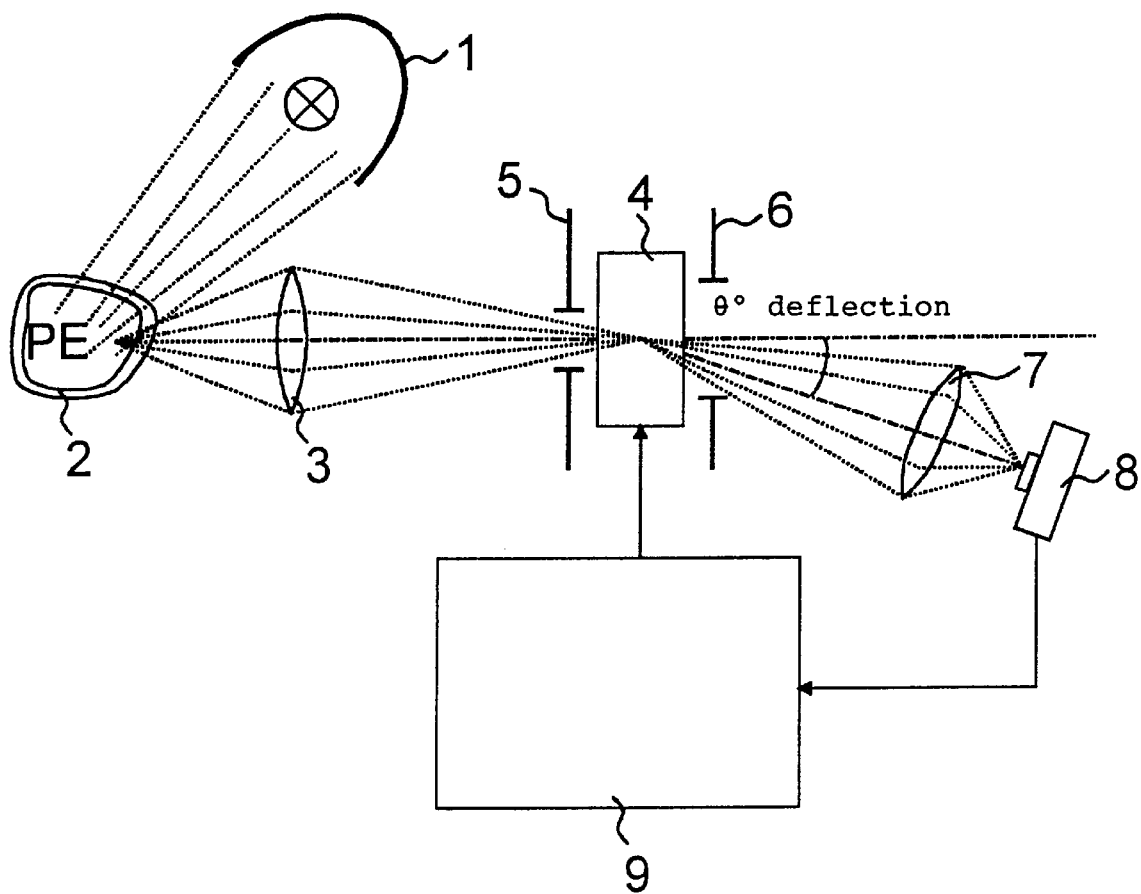
FIG. 4: a schematic view of a device for recognizing organic substances.

FIG. 4 shows the schematic structure of a device for recognizing organic substances according to the invention. A light source 1 consisting of a halogen lamp and an ellipsoid reflector, with a power of e.g. 250 watts directly irradiates a sample 2 to be investigated, containing an organic substance, whose property with reference to its absorption spectrum can be established in the range between 2–4 $\mu$m. Instead of the halogen lamp, for example a surface irradiator of stainless steel operating at about 600–1000° C. could be used. The distance between the light source 1 and the sample 2 can come to up to 50 cm.

Via a planar-convex lens 3, preferably of $MgF_2$, the light reflected from the sample 2 impinges on an acousto-optical filter 4, which consists of a crystal of $TeO_2$ with a piezo-crystal glued on and serving as an oscillator crystal. The piezo-crystal is energized in a way to be described later by a digitally programmable high frequency source. The frequency of this energization determines the wavelength of the light diffracted out, and its amplitude determines the intensity of diffraction. By correspondingly predetermining the energization frequency of the piezo-crystal, therefore, the wavelength of the radiation transmitted by the acousto-optical filter 4 can be set to optional values within the range of 2–4 $\mu$m.

The lens 3 has for example a focal depth of 100 mm and a distance of 20 cm from the sample 2 and of 16 cm from the entry surface of the filter 4. Diaphragms 5 and 6 in the case of the filter 4 prevent at the inlet and outlet side the occurrence of diffused light from the beam path about the lens 3.

Via a further planar-convex lens 7 made of $MgF_2$, the radiation impinges at the selected wavelength on a detector 8, which generates an analog voltage signal corresponding to the intensity of radiation. The lens 7 has for example a focal depth of 31 mm and a distance of 3.5 cm from the detector 8 and of 27.5 cm from the entry surface of the filter 4.

The detector material is preferably mercury cadmium tellurite with a cut-off wavelength of 4.5 $\mu$m. The active surface of the detector 8 comes to 0.1×0.1 $mm^2$, yet this can be enlarged by a glued-on immersion lens to about 1×1 $mm^2$. The sensitivity of the detector can be clearly increased by a Peltier cooling system; a two-stage Peltier cooling system for example reduces the dark current noise by a factor of three.

Figure 5:
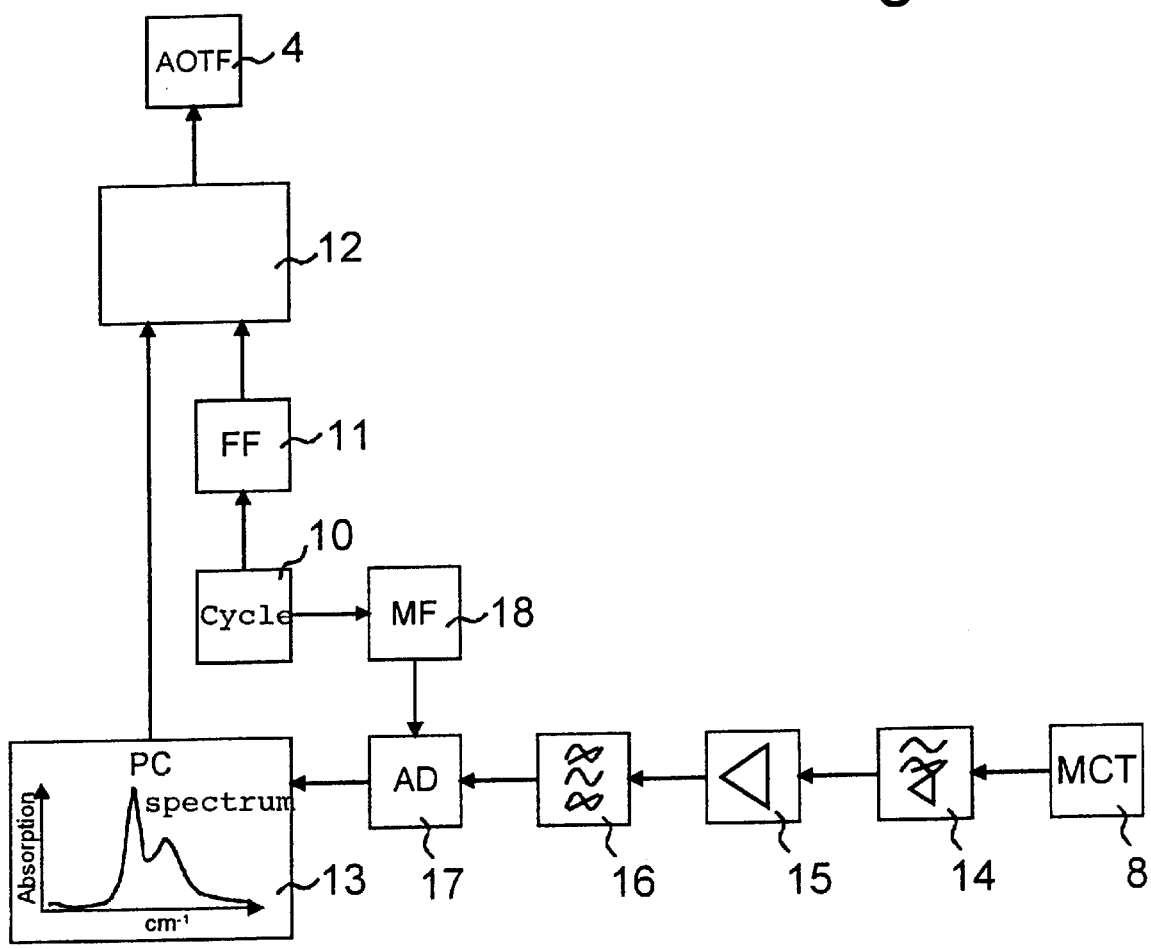
FIG. 5: a block diagram of the filter control and evaluation circuit.

The output signal of the detector 8 is passed to a control and evaluation circuit 9, which is shown in more detail in FIG. 5. A clock generator 10 operated by a quartz oscillator has an output frequency of 50 kHz, which is reduced to 25 kHz by a subsequently-incorporated D-flip-flop 11. The D-flip-flop regulates the output power of a driver circuit 12 for the piezo-crystal of the filter 4 in such a way that switch-over is carried out between power zero and full power at a cycle ratio of 1:1. The desired driver frequency for the piezo-crystal is set by corresponding programming of a data processing appliance 13, for example a PC, in the driver circuit 12.

The analog voltage signal obtained at the output of the detector 8 corresponds to the intensity of radiation of the wave-length diffracted out. This signal is firstly amplified in a pre-amplifier with high-band-pass filter 14, and the direct voltage (off-set voltage) of the signal is separated by the high-band-pass filter. A final amplifier 15 consisting of two cascaded electrometer amplifiers amplifies the signal to about 5 volts.

A band-pass filter 16, preferably with an amplification of 10 at the modulation frequency of light (here 25 kHz) filters the signal and separates out undesired noise or disturbance signals, the signal thus obtained is now digitised in a A/D-converter 17 (12-bit resolution) and is stored in the data processing appliance 13.

A monoflop 18 triggered by the clock generator 10 passes a trigger signal at a predetermined time delay to the A/D-converter 17, so that at the moment of conversion, precisely the peak value of the signal is obtained.

Figure 6:
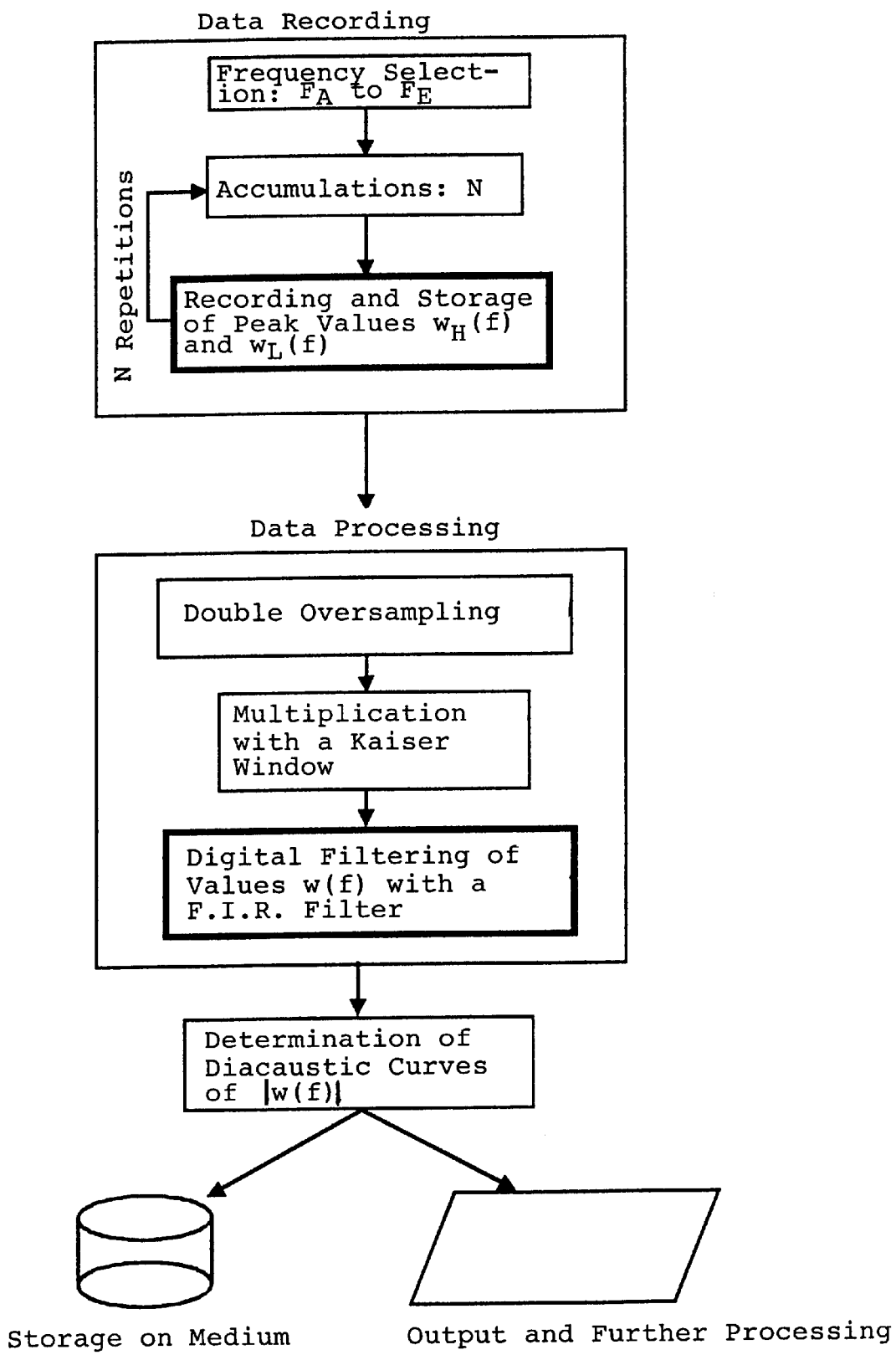
FIG. 6: a flow diagram showing the process of data recording and data processing.

The embodiment of the method as software in the data processing appliance 13 is explained in the following with reference to FIG. 6. Firstly the start and end frequency fA or fE of the area to be scanned and the number of accumulations, i.e. scanning cycles, are input into the appliance. Now recording of the data obtained by scanning can begin. The positive and negative peak values of the spectral signal w(f) are recorded at the corresponding driver frequency f, then the frequency is advanced by one step. After the values w(f) have been recorded for all frequencies, this procedure starts anew and is repeated in accordance with the selected number of accumulations.

Thereafter the recorded data are processed. Firstly an average value is calculated and inserted between each value w(f) and w(f+1) of two successive accumulations. This over-sampling leads to a doubling of the scanning frequency. Then the data set obtained is multiplied by a Kaiser window and filtered through a FIR filter. By means of this measure, aliasing effects are intended to be suppressed.

In the last step the diacaustic curve of the values w(f) are determined. The positive and negative peak values of each respective frequency are derived from one another, so that an average is obtained, by means of which an amplitude is precisely associated with each frequency.

The data determined in this manner are stored and/or output for further processing.

What is claimed is:

1. Method of recognizing organic substances in solid bodies by spectral detection of radiation reflected or transmitted by the substances, characterized in that a wavelength range of about 2–4 $\mu$m is used for radiation, and an unmodulated radiation is used to irradiate the solid body.

2. Method according to claim 1, characterized in that a radiation source with an output power of at least 50 watts is used.

3. Method according to claim 1, characterized in that the solid body is directly irradiated by illumination optics and the distance between the illumination optics and the solid body comes to at least 10 cm.

4. Method according to claim 1, characterized in that the irradiated surface on the solid body comes to at least 1 cm$^2$.

5. Method according to claim 1, characterized in that the solid bodies are moved past illumination optics.

6. Method according to claim 1, characterized in that the recognition is carried out with reference to absorption bands of extension oscillations of C—H-bonds and extension oscillations of any N—H-bonds present.

7. Method according to claim 1, characterized in that the substances to be recognized are plastics.

8. Method according to claim 7, characterized in that the substances to be recognized are plastics.

9. Method according to claim 1, characterized in that the substances to be recognized are surface coatings.

10. Method according to claim 1, characterized in that, in order to irradiate the substances to be recognized a wide-band radiation is used, and in that the reflected or transmitted radiation is passed through a narrow-band filter.

11. Method according to claim 10, characterized in that a transmittance frequency of the narrow-band filter is altered.

12. Device for carrying out the method according to claim 1, characterized in that, in order to screen out the wavelength range from about 2–4 $\mu$m from the radiation reflected or transmitted by the solid body, an acousto-optical filter is located between the solid body and a detector.

13. Device according to claim 12, characterized in that the acousto-optical filter consists of a TeO$_2$-crystal, to which is secured a piezo-crystal.

14. Device according to claim 13, characterized in that the piezo-crystal may be energized, in order to pass through the wavelength range of about 2–4 $\mu$m, by a digitally programmable high frequency source.

15. Device according to claim 14, characterized in that the high frequency source for the piezo-crystal can be operated in a cycled fashion.

16. Method according to claim 15, character in that the cycle frequency comes to 25 kHz.

17. Device according to claim 12, characterized in that the detector consists of mercury cadmium tellurite, and has a cut-off wavelength of about 4.5 $\mu$m.

18. Device according to claim 17, characterized in that the detector is provided with a Peltier cooling system.

19. Device according to claim 12, characterized in that the output signal of the detector, is filtered by a band-pass filter, which is in a fixed relationship with the cycle for the piezo-crystal.

* * * * *